United States Patent
Kim et al.

(10) Patent No.: US 9,504,271 B2
(45) Date of Patent: Nov. 29, 2016

(54) METHOD FOR STERILIZING MICROBIAL CELLS USING POLYETHYLENE GLYCOL-BASED NONIONIC SURFACTANT

(71) Applicant: CJ CHEILJEDANG CORPORATION, Seoul (KR)

(72) Inventors: Jin Ha Kim, Bucheon-si (KR); Young Mi Lee, Bucheon-si (KR); Seong Bo Kim, Seoul (KR); Taek Beom Kim, Seoul (KR); Yang Hee Kim, Bucheon-si (KR); Seung Won Park, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/311,185

(22) Filed: Jun. 20, 2014

(65) Prior Publication Data

US 2014/0302564 A1 Oct. 9, 2014

Related U.S. Application Data

(63) Continuation-in-part of application No. PCT/KR2012/011161, filed on Dec. 20, 2012.

(30) Foreign Application Priority Data

Dec. 23, 2011 (KR) .......................... 10-2011-0141641

(51) Int. Cl.

| | | |
|---|---|---|
| *A23L 1/03* | (2006.01) | |
| *C12N 1/20* | (2006.01) | |
| *C12N 9/90* | (2006.01) | |
| *C12N 11/16* | (2006.01) | |
| *A23L 3/3508* | (2006.01) | |
| *C12P 19/02* | (2006.01) | |
| *C12P 19/24* | (2006.01) | |

(52) U.S. Cl.

CPC ............ *A23L 1/0345* (2013.01); *A23L 3/3508* (2013.01); *A23L 29/065* (2016.08); *C12N 1/20* (2013.01); *C12N 9/90* (2013.01); *C12N 11/16* (2013.01); *C12P 19/02* (2013.01); *C12P 19/24* (2013.01); *C12Y 503/01003* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 3,912,450 A | 10/1975 | Boucher | |
| 5,514,574 A * | 5/1996 | Kitatsuji | C12N 9/12 435/189 |
| 5,863,547 A | 1/1999 | Miner | |
| 7,393,528 B2 | 7/2008 | Tvdten | |
| 7,658,959 B2 | 2/2010 | Koefod et al. | |
| 2010/0041106 A1 | 2/2010 | Kim et al. | |

FOREIGN PATENT DOCUMENTS

| | | | |
|---|---|---|---|
| CN | 101631856 A | | 1/2010 |
| EP | 1233057 A1 | | 8/2002 |
| JP | 50048193 | * | 4/1975 |
| JP | 56113294 | * | 9/1981 |
| JP | 2006-050931 | | 2/2006 |
| JP | 2010510774 A | | 4/2010 |
| KR | 1020040035683 A | | 4/2004 |
| KR | 100501864 B1 | | 7/2005 |
| WO | 01/36592 A1 | | 5/2001 |
| WO | 2008/066260 A1 | | 6/2008 |

OTHER PUBLICATIONS

Chirife, Jorege et al. "In Vitro Antibacterial Activity of Concentrated Polyethylene Glycol 400 Solutions", Antimicrobial Agents and Chemotherapy, Sep. 1983, p. 409-412.
International Search Report dated Apr. 26, 2013 for PCT/KR1012/011161.
Extended European Search Report dated Mar. 7, 2015 of corresponding European Patent Application No. 12858874.6—9 pages.

* cited by examiner

*Primary Examiner* — Suzanne M Noakes
(74) *Attorney, Agent, or Firm* — Knobbe Martens Olson & Bear LLP

(57) ABSTRACT

A method for sterilizing microbial cells is provided. According to the method, microbial cells or a culture containing microbial cells are treated with a polyethylene glycol-based nonionic surfactant so that almost all of the microbial cells are sterilized while the enzyme activity expressed in the microbial cells is maintained at a high level. A method for sterilizing microbial cells and a material containing the sterilized microbial cells, in which the microbial cells are sterilized using a polyethylene glycol-based nonionic surfactant, can be used for foods so that the microbial cells are sterilized to be used in food production. Further, a material containing sterilized microbial cells can be used in processes for preparing tagatose, in which *Corynebacterium* genus microbial cells that produce Galactose and/or Arabinose isomerase are sterilized using a polyethylene glycol-based nonionic surfactant.

15 Claims, 1 Drawing Sheet

METHOD FOR STERILIZING MICROBIAL CELLS USING POLYETHYLENE GLYCOL-BASED NONIONIC SURFACTANT

BACKGROUND

Technical Field

The present invention relates to a method for sterilizing microbial cells by treating microbial cells or cultures containing microbial cells with a polyethylene glycol-based nonionic surfactant to achieve substantially complete sterilization of the microbial cells while maintaining enzyme activity expressed in the microbial cells at a high level, and sterilized microbial cells produced therefrom.

More particularly, the present invention relates to a method for sterilizing microbial cells by treating microbial cells with a polyethylene glycol-based nonionic surfactant which can be used in foods, thereby enabling use of the sterilized microbial cells for food production, and a substance containing the sterilized microbial cells.

Background Art

Some processes for preparing foods may require the use of various enzymes produced by various microorganisms. Namely, an intended enzyme may be obtained from a microorganism and then used as a constitutional material for foods.

As such, in the event of employing microorganism cells in the process of food production, there are problems in that viable microorganism cells can be leaked and incorporated into products, thereby causing secondary microorganism contamination.

To resolve these problems, such leakage of microbial cells is generally minimized by reacting microorganisms having high stability in a closed system and fixing the used microbial cells. In recent years, however, the use of genetically engineered microorganisms has been rapidly increased for mass production of specific enzymes. When such genetically engineered microorganisms are used in the process of food production, a complete sterilization of the microorganism cells is required to ensure food safety.

Methods for completely sterilizing microorganism cells are largely classified into two methods, i.e., a method using physical means and a method using chemical means. Examples of the method using the physical means may include methods of performing heating, ultraviolet irradiation, electromagnetic wave irradiation, sterilization filtration, or the like. Examples of the method using the chemical means may include methods using phenols, alcohols, oxidants, heavy metal ions, sterilization gases, or the like.

Korean Patent No. 10-0501864 discloses one example of a method for sterilizing microbial cells using chemical means.

This publication discloses a method for sterilizing *Rhodococcus*, which is a recombinant bacteria, using a cationic or an amphoteric surfactant. This method improves sterilization efficiency of microbial cells using a cationic surfactant. However, this method has a problem caused by benzethonium chloride used as a cationic surfactant.

Benzethonium chloride has strong sterilizing power and is used in medicines for treating rhinitis and stomatitis, mouthwash, and the like. However, recent studies report that benzethonium chloride is considered a representative environmental hormone causing endocrine disruption and is quite noxious to the human body.

Accordingly, the above method can be only employed in a method for sterilizing microbial cells for industrial purposes without risk of being introduced to the human body in specific applications. In this regard, the above method is far from a method for sterilizing microbial cells, which can be used for food production as suggested in at least some embodiments of the present invention.

The foregoing discussions in this section are to provide general background information and do not constitute an admission of prior art.

SUMMARY

One aspect of the invention relates to a method for sterilizing microbial cells, comprising treating microbial cells or cultures containing microbial cells with a polyethylene glycol-based nonionic surfactant. In some embodiments, the polyethylene glycol-based nonionic surfactant may comprise at least one selected from the group consisting of ether type, ester type and nitrogen-containing type polyethylene glycol-based nonionic surfactants. In some other embodiments, the polyethylene glycol-based nonionic surfactant may be used in a concentration of 0.1% to 10% based on a weight of the microbial cells or the cultures containing the microbial cells. According to certain embodiments, the treatment may be performed at a temperature ranging from 0° C. to 70° C. In certain some embodiments, the microbial cells may be of genus *Corynebacterium*. The genus *Corynebacterium* may have a capability of producing galactose and/or arabinose isomerase at least in some embodiments. In addition, the method can be employed in a process for preparing tagatose at least in some embodiments.

In another aspect of the invention, a substance containing sterilized microbial cells sterilized by any of the methods according to various embodiments of the invention is provided. In some embodiments, the sterilized microbial cells may be used for preparation of tagatose.

In still another aspect of the invention, a substance containing sterilized microbial cells, which may be capable of being used for food production, is provided. The substance may comprise a) a polyethylene glycol-based nonionic surfactant and b) galactose or arabinose isomerase. In certain embodiments, the sterilized microbial cells may be of genus *Corynebacterium*. In some embodiments, the sterilized microbial cells may be sterilized by any of the methods according to various embodiments of the invention.

In still another aspect of the invention, a method of producing tagatose is provided. According to some embodiments, the method may comprise providing microbial cells comprising enzymes, which comprise galactose isomerase and arabinose isomerase, contacting the microbial cells with a nonionic surfactant comprising a polyethylene glycol-moiety to sterilize at least part of the microbial cells and to cause at least part of the enzymes to be released from the microbial cells, separating at least part of the released enzymes from the microbial cells, and mixing at least one of galactose and arabinose with at least part of the separated enzymes to cause to produce tagatose. According to some embodiments, the nonionic surfactant may be selected from the group consisting of polyoxyethylene, polyethylene glycol fatty acid ester, polyoxyethylene fatty acid amide and polyoxyethylene stearylamine. In certain embodiments, the nonionic surfactant may comprise polyoxyethylene stearylamine. In some other embodiments, contacting may comprise mixing, with the microbial cells, the nonionic surfactant in a concentration of 0.1% to 10% based on a weight of the microbial cells. In still some other embodiments, contacting may comprise mixing, with the microbial cells, the nonionic surfactant in a concentration of 1% to 8% based on a weight of the microbial cells. Further, in some embodiments, the microbial cells may be of genus *Corynebacterium*. In certain some embodiments, the microbial cells may comprise microbial cells of *Corynebacterium glutamicum* ATCC 13032.

DETAILED DESCRIPTION OF EMBODIMENTS

Figure 1:
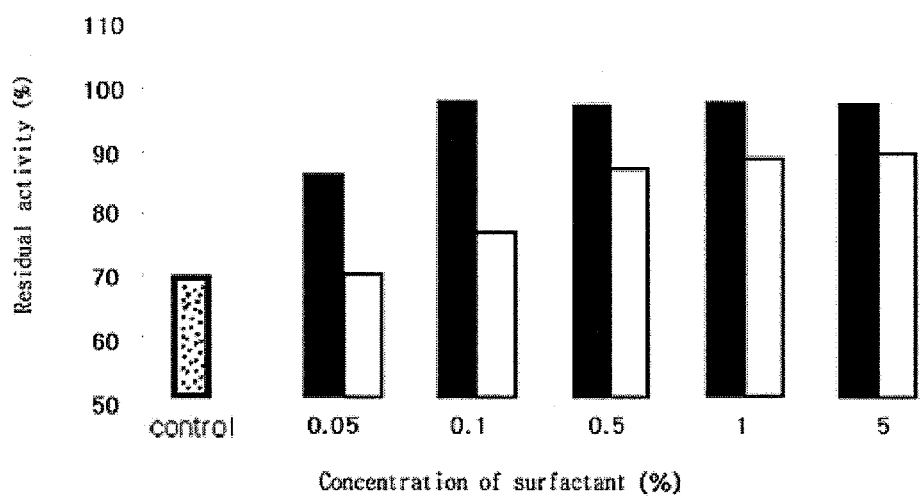
FIG. 1 is a graph depicting results of residual enzyme activity after microbial cells were sterilized at 30° C. in Example 2.
Figure 2:
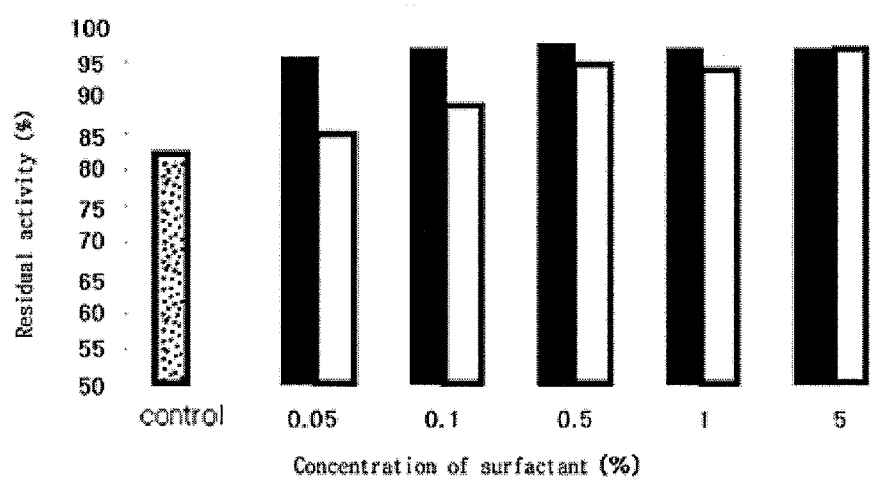
FIG. 2 is a graph depicting results of residual enzyme activity after microbial cells were sterilized at 50° C. in Example 2.

The inventors of the present invention conducted thorough investigation in order to solve the problems as described above, and developed a method for sterilizing microbial cells using a polyethylene glycol-based nonionic surfactant which can be used in foods.

Specifically, one aspect of the present invention is aimed at providing a method for sterilizing microbial cells by treating microbial cells or cultures containing microbial cells with a polyethylene glycol-based nonionic surfactant such that the microbial cells are substantially completely sterilized while enzyme activity expressed in the microbial cells is maintained at a high level.

In addition, another aspect of the present invention is aimed at providing a substance containing sterilized microbial cells, which is capable of being used for food production by treating microbial cells with a polyethylene glycol-based nonionic surfactant.

Further, another aspect of the present invention is aimed at providing a substance containing sterilized microbial cells, which is capable of being used for tagatose production by treating genus *Corynebacterium* microbial cells, which produce galactose and/or arabinose isomerase, with a polyethylene glycol-based nonionic surfactant.

Embodiments of the present invention relates to a method for sterilizing microbial cells by treating microbial cells with a polyethylene glycol-based nonionic surfactant, and a substance containing the sterilized microbial cells.

In accordance with one aspect of the present invention, there is provided a method for sterilizing microbial cells, which includes treating microbial cells or cultures containing microbial cells with a polyethylene glycol-based nonionic surfactant.

In one embodiment of the invention, the polyethylene glycol-based nonionic surfactant includes at least one selected from the group consisting of ether type, ester type and nitrogen-containing type polyethylene glycol-based nonionic surfactants.

In another embodiment of the invention, the polyethylene glycol-based nonionic surfactant is used in a concentration of 0.1% to 10% based on the microbial cells or cultures containing the microbial cells.

In a further embodiment of the invention, treatment of the microbial cells or cultures containing the microbial cells is performed at a temperature from 0° C. to 70° C.

In yet another embodiment of the invention, the microbial cell is genus *Corynebacterium*.

In yet another embodiment of the invention, the microbial cell is genus *Corynebacterium* capable of producing galactose and/or arabinose isomerase.

In yet another embodiment of the invention, the method is employed in a process for preparing tagatose.

Yet another embodiment of the present invention provides a substance containing sterilized microbial cells which are sterilized by the method of the present invention.

In accordance with another aspect of the present invention, there is provided a substance containing the sterilized microbial cells, wherein the sterilized microbial cells are used for preparation of tagatose.

In accordance with a further aspect of the present invention, there is provided a substance containing sterilized microbial cells, which is capable of being used for food production and includes: a) a polyethylene glycol-based nonionic surfactant; and b) galactose or arabinose isomerase.

In the method for sterilizing microbial cells according to certain embodiments of the present invention, microbial cells or cultures containing microbial cells are treated with a polyethylene glycol-based nonionic surfactant, thereby achieving substantially complete sterilization of the microbial cells while allowing enzyme activity expressed in the microbial cells to be maintained at a high level.

In addition, according to some embodiments of the present invention, the method for sterilizing microbial cells prevents secondary contamination of products due to leakage of microbial cells in preparation of foods and facilitates treatment of the microbial cells in a subsequent process.

Further, some embodiments of the present invention provide a substance containing sterilized microbial cells, which is capable of being used for food production, by sterilizing microbial cells with a polyethylene glycol-based nonionic surfactant which can be used in foods.

Furthermore, some embodiments of the present invention provide a substance containing sterilized microbial cells, which is capable of being used for food production, by sterilizing genus *Corynebacterium* microbial cells capable of producing galactose and/or arabinose isomerase with a polyethylene glycol-based nonionic surfactant.

Hereinafter, embodiments of the present invention will be described in more detail with reference to the accompanying drawings. A description of details apparent to those skilled in the art will be omitted herein.

In accordance with one aspect of the invention, there is provided a method for sterilizing microbial cells, which includes treating microbial cells or cultures containing microbial cells with a polyethylene glycol-based nonionic surfactant.

Microbial cells used in some embodiments of the present invention are not particularly limited, and any well-known microorganisms including wild types and genetically engineered microorganisms can be used.

The microbial cells preferably include genus *Corynebacterium* microbial cell, more preferably *Corynebacterium glutamicum* ATCC 13032.

*Corynebacterium glutamicum* ATCC 13032 is known in the art and deposited with an international depository authority, the ATCC (American Type Culture Collection, Manassas, USA).

*Corynebacterium glutamicum* ATCC 13032, which can be used in some embodiments of the present invention, may have a capability of producing galactose and/or arabinose isomerase and may be genetically recombined to produce the isomerase.

As used herein, the cultures may refer to a culture medium or a culture solution in which microbial cells are cultivated, and a culture containing a cultivation resultant of microbial cells in the culture medium or culture solution.

The cultures may include nutrition sources required in culturing microbial cells, for example, a carbon source, a nitrogen source and the like, as well as mineral salt components, amino acids, vitamins, nucleic acids and/or other components generally contained in culture media (or culture solutions).

Further, the cultures may include enzymes produced and secreted from microbial cells as resultants of culturing the microbial cells.

As used herein, the term "sterilizing microbial cells" means that the viable microbial cell count of the corresponding microbial cells in a relatively high concentration of microbial cell suspension is substantially close to 0. The expression "substantially close to 0" means that the survival rate of microbial cells (viable microbial cell count after sterilization/viable microbial cell count before sterilization) is $1/10^5$ or less.

The viable microbial cell count may be calculated by diluting a microbial cell suspension to a predetermined concentration, spreading the microbial cell suspension on a culture medium in which the microbial cells are viable, and determining the viable microbial cell count on the culture medium based on the dilution ratio.

The method for sterilizing microbial cells according to some embodiments of the present invention includes treating microbial cells or cultures containing microbial cells with a polyethylene glycol-based nonionic surfactant. The expression "treating with a polyethylene glycol-based nonionic surfactant" means all forms of treatment, for example, by directly contacting the microbial cells with the polyethylene glycol-based nonionic surfactant, or by contacting a culture containing the microbial cells with the polyethylene glycol-based nonionic surfactant added. Sterilization may be performed while stirring the surfactant.

In certain embodiments of the present invention, the polyethylene glycol-based nonionic surfactant may be used without limitation in so far as the nonionic surfactant is a polyethylene glycol-based surfactant.

Examples of the polyethylene glycol-based nonionic surfactant may include ether type polyethylene glycol-based nonionic surfactants, such as polyoxyethylene and the like; ester type polyethylene glycol-based nonionic surfactants, such as polyethylene glycol fatty acid ester and the like; or nitrogen-containing type polyethylene glycol-based nonionic surfactants, such as polyoxyethylene fatty acid amide, polyoxyethylene stearylamine and the like, without being limited thereto. These may be used alone or in combination of two or more thereof.

In some embodiments of the present invention, the polyethylene glycol-based nonionic surfactant is preferably a nitrogen-containing type nonionic surfactant, such as polyoxyethylene fatty acid amide and polyoxyethylene stearylamine (POESA).

In treatment of microbial cells or cultures containing microbial cells with the polyethylene glycol-based nonionic surfactant, the concentration of the surfactant is not particularly limited. Preferably, the concentration of the surfactant is 0.1% to 10% (w/w), more preferably 0.5% to 8%, for example 1% to 8% based on the weights of the microbial cells or cultures containing the microbial cells.

When the concentration of the surfactant used is less than 0.1%, it is difficult to achieve sufficient sterilization of microbial cells. When the concentration of the surfactant used is greater than 10%, the amount of surfactant becomes excessive, which is not efficient, and there is a possibility of deteriorating enzyme activity. Further, the content of the surfactant in the sterilized microbial cells increases, so that the sterilized microbial cells become unsuitable for use in various applications, such as food production and the like.

The method for sterilizing microbial cells according to some embodiments of the present invention may be carried out at any temperature so long as the temperature does not inhibit stability of enzymes produced by the microbial cells. Preferably, the method for sterilizing microbial cells is performed at a temperature from 0° C. to 70° C., more preferably from 10° C. to 60° C.

When the temperature is less than 0° C. or greater than 70° C., the enzymes produced by the microbial cells can be deteriorated, thereby lowering enzyme activity.

According to one aspect of the present invention, the method may further include adding a substrate for the enzymes and/or a substrate analogue in order to maintain stability of the enzymes produced by the corresponding microbial cells without deteriorating enzyme activity.

In another aspect of the present invention, the method may be used in a process of producing tagatose.

In accordance with a further aspect of the invention, there is provided a substance containing the sterilized microbial cells which are sterilized by the method according to the present invention.

The substance containing the sterilized microbial cells may include the sterilized microbial cells and enzymes produced by the microbial cells before sterilization.

The substance containing the sterilized microbial cells may be prepared by sterilizing genus *Corynebacterium* microbial cells, preferably *Corynebacterium glutamicum* microbial cells, more preferably *Corynebacterium glutamicum* ATCC 13032 microbial cells capable of producing galactose and/or arabinose isomerase.

The substance containing the sterilized microbial cells may include galactose and/or arabinose isomerase.

The use of the substance containing the sterilized microbial cells is not particularly limited, and the substance containing the sterilized microbial cells may be used for food production, preferably in the process of producing tagatose.

Tagatose is an isomer of galactose and is a natural sugar known to have physical and chemical properties similar to those of fructose.

Tagatose is recognized as GRAS (Generally Recognized As Safe) by the FDA (Food and Drug Administration) and is approved for use as a sweetener for foods, drinks, health foods, diet additives, and the like. Tagatose has no side effects and is a low calorie sugar having almost zero calories. Tagatose is an important sweetener substituting sugar which is one factor causing various adult diseases such as obesity, diabetes, and the like.

Tagatose may be prepared through a biological method by isomerizing galactose or arabinose using galactose or arabinose isomerase.

According to a further aspect of the present invention, there is provided a substance containing sterilized microbial cells, which is capable of being used for food production, and includes: a) a polyethylene glycol-based nonionic surfactant; and b) galactose or arabinose isomerase.

As used herein, the term "food production" may include all cases where the substance containing sterilized microbial cells is used directly or indirectly in food production.

Next, at least some embodiments of the present invention will be described in more detail with reference to examples and comparative examples. However, it should be understood that the following examples and comparative examples are provided for illustration only and are not to be construed in any way as limiting the scope of the present invention.

Example 1

Sterilization of Microbial Cells Depending Upon Concentration of Polyethylene Glycol-Based Nonionic Surfactant Recombinant *Corynebacterium glutamicum* ATCC 13032 strains were treated with different concentrations of a polyoxyethylene stearylamine (POESA) as nitrogen-containing polyethylene glycol-based surfactant (Naimine S-215, Nihon Yushi Co., Ltd.) and Tween 80 (polyoxyethylene sorbitan mono-oleate) provided as nonionic surfactants to determine the degree of sterilization of *Corynebacterium glutamicum* ATCC 13032 and enzyme activity. A detailed method for performing such measurement is as follows.

(1) Cultivation of *Corynebacterium glutamicum* ATCC 13032

MB medium (10 g/L of Bacto-trypton, 5 g/L of Bacto-yeast extract, 5 g/L of NaCl, 5 g/L of Soytone) containing kanamycin in a concentration of 10 μg/ml was inoculated with *Corynebacterium glutamicum* ATCC 13032 such that the initial concentration O.D. 600 was 0.1, followed by culturing at 30° C. for 24 hours to induce expression of recombinant galactose isomerase.

A 5 L jar fermenter containing 3 L of a mutation medium (80 g/L of glucose, 20 g/L of soytone, 10 g/L of $(NH_4)_2SO_4$, 1.2 g/L of $KH_2PO_4$, 1.4 g/L of $MgSO_4$) containing kanamycin in a concentration of 10 μg/ml was inoculated with the resulting culture solution such that O.D. 600 was 0.6, followed by culturing at 30° C. for 20 hours.

(2) Sterilization of Microbial Cells 11 specimens composed of 40 ml of cultures containing the microbial cells were prepared. A surfactant was not added to a first specimen, a polyethylene glycol-based nonionic surfactant (POESA) was added in various concentrations (based on the weights of the cultures, 0.05%, 0.1%, 0.5%, 1% and 5%, respectively) to second to sixth specimens, and Tween 80 was added in various concentrations to seventh to eleventh specimens, followed by leaving the microbial cells at 30° C. for 3 hours to sterilize the microbial cells.

(3) Determination of Viable Microbial Cell Count

After the sterilization of the microbial cells, the 11 specimens were applied to MB agar medium containing kanamycin, followed by culturing at 30° C. for 24 hours to determine the viable microbial cell count.

(4) Measurement of Enzyme Activity

A culture containing sterilized microbial cells (a substance containing sterilized microbial cells) was subjected to centrifugation at 8000×g (=10,000 rpm) for 10 minutes to harvest the microbial cells. Cultures free from the microbial cells were suspended in 50 mM Tris-HCl buffer solution (purchased from Sigma-Aldrich) containing 300 g/L of galactose substrate, pH 7.5, followed by isomerization from galactose to tagatose at 55° C. for 2 hours.

After the isomerization, residual activity of the galactose isomerase was measured.

Enzyme activity after the sterilization treatment was measured by comparing the produced amount of tagatose after the completion of reaction with the amount of galactose at the start of isomerization.

After the sterilization, the viable microbial cell count and residual enzyme activity were measured. Results are shown in Table 1.

TABLE 1

| Surfactant | Treatment Temperature (° C.) | Treatment time (h) | Viable microbial cell count (number/ml) | Residual enzyme activity (%) |
|---|---|---|---|---|
| None | 30 | 3 | >$10^8$ | 68 |
| POESA 0.05% | | | >$10^8$ | 87 |
| POESA 0.1% | | | >$10^7$ | 98 |
| POESA 0.5% | | | >$10^4$ | 96 |
| POESA 1% | | | 0 | 97 |
| POESA 5% | | | 0 | 100 |
| Tween 80 0.05% | | | >$10^8$ | 71 |
| Tween 80 0.1% | | | >$10^8$ | 80 |
| Tween 80 0.5% | | | >$10^8$ | 91 |
| Tween 80 1% | | | >$10^8$ | 93 |
| Tween 80 5% | | | >$10^8$ | 92 |

Example 2

Sterilizing of Microbial Cells Using Polyethylene Glycol-Based Nonionic Surfactant Depending on Temperature Change Sterilization was performed by the same procedure as in Example 1 except that two specimens for each condition were prepared with the sort and concentration of the surfactant varied to prepare 22 specimens and that the temperature for sterilization treatment was set to 30° C. and 50° C.

After the sterilization, the viable microbial cell count and residual enzyme activity were measured. Results are shown in Tables 2 and 3.

TABLE 2

| Surfactant | Treatment Temperature (° C.) | Treatment time (h) | Viable microbial cell count (number/ml) | Residual activity of enzyme (%) |
|---|---|---|---|---|
| None | 30 | 3 | >$10^8$ | 68 |
| | 50 | | >$10^7$ | 87 |
| POESA 0.05% | 30 | | >$10^8$ | 87 |
| | 50 | | >$10^4$ | 95 |
| POESA 0.1% | 30 | | >$10^7$ | 98 |
| | 50 | | >$10^4$ | 98 |
| POESA 0.5% | 30 | | >$10^4$ | 96 |
| | 50 | | 30 | 96 |
| POESA 1% | 30 | | 0 | 97 |
| | 50 | | 0 | 95 |
| POESA 5% | 30 | | 0 | 100 |
| | 50 | | 0 | 96 |

TABLE 3

| Surfactant | Treatment Temperature (° C.) | Treatment time (h) | Viable microbial cell count (number/ml) | Residual activity of enzyme (%) |
|---|---|---|---|---|
| Tween 80 0.05% | 30 | 3 | >$10^8$ | 71 |
| | 50 | | >$10^8$ | 90 |
| Tween 80 0.1% | 30 | | >$10^8$ | 80 |
| | 50 | | >$10^7$ | 93 |
| Tween 80 0.5% | 30 | | >$10^8$ | 91 |
| | 50 | | >$10^5$ | 97 |
| Tween 80 1% | 30 | | >$10^8$ | 93 |
| | 50 | | >$10^3$ | 97 |

TABLE 3-continued

| Surfactant | Treatment Temperature (° C.) | Treatment time (h) | Viable microbial cell count (number/ml) | Residual activity of enzyme (%) |
|---|---|---|---|---|
| Tween 80 5% | 30 | | >10$^8$ | 92 |
| | 50 | | >10$^3$ | 97 |

As shown in Tables 1 to 3, it could be seen that, when Tween 80 was used, the microbial cells were not completely sterilized even with treatment using 5% Tween 80. However, when the polyethylene glycol-based nonionic surfactant was used, the viable microbial cell count started to remarkably decrease from the concentration of 0.5% and the microbial cells were completely sterilized at a concentration of 1%.

Further, it could be seen that sterilization with the polyethylene glycol-based nonionic surfactant exhibited higher residual enzyme activity as compared with the case where sterilization was performed with Tween 80 in the same concentration. From the result that enzyme activity was higher upon sterilization using the polyethylene glycol-based nonionic surfactant than the case where the enzyme was not treated with the surfactant, it was determined that the surfactant could facilitate interaction between enzyme and substrate.

The measurement results at different sterilization temperatures showed that sterilization was performed more effectively when microbial cells were treated at 50° C.

What is claimed is:

1. A method for sterilizing microbial cells, the method comprising:
    cultivating microbial cells comprising genus *Corynebacterium* in a culture such that O.D. 600 becomes at least 0.6; and
    subsequently, adding to the culture an amount of polyoxyethylene fatty acid amide to effectively sterilize the microbial cells to a survival rate of 10$^{-5}$ or less, wherein the amount is in a concentration of 0.5 to 8% w/w with reference to the culture.

2. The method according to claim 1, wherein the polyoxyethylene fatty acid amide comprises polyoxyethylene stearylamine (POESA), wherein the genus *Corynebacterium* comprises *glutamicum* ATCC 13032.

3. The method according to claim 1, wherein the concentration is 1 to 8% w/w with reference to the culture.

4. The method according to claim 1, wherein adding is performed at a temperature within a range from 0° C. to 70° C.

5. The method according to claim 1, wherein the genus *Corynebacterium* produces at least one isomerase, wherein adding the polyoxyethylene fatty acid amide to effectively sterilize the microbial cells while substantially maintaining enzymatic activities of the at least one isomerase.

6. The method according to claim 5, wherein the enzymatic activities are maintained over 95%.

7. The method according to claim 1, wherein the genus *Corynebacterium* comprises *glutamicum* ATCC 13032, which produces galactose isomerase and the arabinose isomerase in the culture, wherein adding the polyoxyethylene fatty acid amide to effectively sterilize the microbial cells while substantially maintaining enzymatic activities of the galactose isomerase and the arabinose isomerase produced by the microbial cells.

8. A method of producing galactose isomerase and arabinose isomerase, the method comprising:
    cultivating the microbial cells and sterilizing the microbial cells according to the method of claim 1, in which the microbial cells produce galactose isomerase and arabinose isomerase into the culture; and
    subsequently, separating at least part of the galactose isomerase and the arabinose isomerase from the culture.

9. The method according to claim 1, wherein cultivating is at least for 20 hours.

10. A method of producing tagatose, the method comprising:
    producing galactose isomerase and arabinose isomerase according to the method of claim 8; and
    mixing at least one of galactose and arabinose with at least part of the separated galactose isomerase and arabinose isomerase to produce tagatose.

11. The method according to claim 10, wherein the polyoxyethylene fatty acid amide comprises polyoxyethylene stearylamine (POESA).

12. The method according to claim 10, wherein the the concentration is 1 to 8% w/w with reference to the culture.

13. The method according to claim 10, wherein the genus *Corynebacterium* produces galactose isomerase and the arabinose isomerase in the culture, wherein adding the polyoxyethylene fatty acid amide to effectively sterilize the microbial cells while substantially maintaining enzymatic activities of the galactose isomerase and the arabinose isomerase produced by the microbial cells.

14. The method according to claim 10, wherein the enzymatic activities are maintained over 95%.

15. The method according to claim 11, wherein the genus *Corynebacterium* comprises *Corynebacterium glutamicum* ATCC 13032.

* * * * *

UNITED STATES PATENT AND TRADEMARK OFFICE
CERTIFICATE OF CORRECTION

PATENT NO. : 9,504,271 B2
APPLICATION NO. : 14/311185
DATED : November 29, 2016
INVENTOR(S) : Kim et al.

It is certified that error appears in the above-identified patent and that said Letters Patent is hereby corrected as shown below:

In the Specification

In Column 7 at Line 19, change "trypton," to --tryptone,--.

In the Claims

In Column 10 at Line 36, in Claim 12, change "the the" to --the--.

Signed and Sealed this
Eleventh Day of April, 2017

Michelle K. Lee
*Director of the United States Patent and Trademark Office*